US012589254B2

(12) United States Patent
Engman et al.

(10) Patent No.: US 12,589,254 B2
(45) **Date of Patent: *Mar. 31, 2026**

(54) WEARABLE CARDIOVERTER DEFIBRILLATOR WITH AI-BASED FEATURES

(71) Applicant: West Affum Holdings DAC, Dublin (IE)

(72) Inventors: Zoie R. Engman, Kirkland, WA (US); Erick M. Roane, Bellevue, WA (US); Steven E. Sjoquist, Lynnwood, WA (US); Jonathan P. Niegowski, Issaquah, WA (US); Robert R. Buchanan, Bothell, WA (US)

(73) Assignee: West Affum Holdings DAC, Dublin (IE)

( * ) Notice: Subject to any disclaimer, the term of this patent is extended or adjusted under 35 U.S.C. 154(b) by 38 days.

This patent is subject to a terminal disclaimer.

(21) Appl. No.: 18/309,958

(22) Filed: May 1, 2023

(65) Prior Publication Data

US 2023/0264033 A1    Aug. 24, 2023

Related U.S. Application Data

(63) Continuation of application No. 16/946,512, filed on Jun. 24, 2020, now Pat. No. 11,672,996.

(Continued)

(51) Int. Cl.
*A61N 1/39* (2006.01)
*G05B 13/02* (2006.01)

(52) U.S. Cl.
CPC ....... *A61N 1/3904* (2017.08); *G05B 13/0265* (2013.01)

(58) Field of Classification Search
CPC .......................... A61N 1/3904; G05B 13/0265
See application file for complete search history.

(56) References Cited

U.S. PATENT DOCUMENTS 3,724,355 A    4/1973  Busch et al.
3,724,455 A    4/1973  Unger
(Continued)

FOREIGN PATENT DOCUMENTS

DE        2005060985 A2    6/2007
EP          2305110 A1    4/2011
(Continued)

OTHER PUBLICATIONS

Heartstart MRx and XL AED Algorithm-Application Note, Jul. 2001, Edition 2 Philips Healthcare, USA.
(Continued)

*Primary Examiner* — Joseph M Dietrich
(74) *Attorney, Agent, or Firm* — Polsinelli PC

(57) ABSTRACT

"Artificial Intelligence" or "AI" technology can be applied to Wearable Cardioverter Defibrillators ("WCDs") and other wearable medical equipment in various ways, including garment fitting and adjustment, analyzing electrocardiogram ("ECG"), other sensor data and/or other patient data in real time to detect/assess the patient's present condition and/or need for treatment for cardiac and other conditions (e.g., stroke, coughing, apnea, etc.), detect imminent failure of the wearable medical device components, capture and report data collected from the patient for presenting to clinicians, adjust thresholds for alarms and notifications based on patient's responses, improve patient compliance based on the patient's past non-compliant behavior and actions that resulted in the patient becoming compliant, provide tests to the patient, and learn the patient's responses to detect/assess the patient's present condition and/or need for treatment.

20 Claims, 5 Drawing Sheets

SAMPLE COMPONENTS OF WEARABLE CARDIOVERTER DEFIBRILLATOR (WCD) SYSTEM

Related U.S. Application Data

(60) Provisional application No. 62/865,693, filed on Jun. 24, 2019.

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,099,715 B2 | 8/2006 | Korzinov | |
| 7,212,850 B2 | 5/2007 | Prystowsky | |
| 7,559,902 B2 | 7/2009 | Ting et al. | |
| 7,587,237 B2 | 9/2009 | Korzinov | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,907,996 B2 | 3/2011 | Prystowsky | |
| 7,941,207 B2 | 5/2011 | Korzinov | |
| 7,974,689 B2 | 7/2011 | Volpe et al. | |
| 8,024,037 B2 | 9/2011 | Kumar | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,265,432 B2 | 2/2016 | Warren et al. | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,724,008 B2 | 8/2017 | Sullivan et al. | |
| 9,757,581 B2 | 9/2017 | Sullivan et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 11,133,112 B2 | 9/2021 | Teplitzky et al. | |
| 11,672,996 B2 * | 6/2023 | Engman | A61N 1/3904 |
| | | | 607/7 |
| 2002/0181680 A1 | 12/2002 | Linder et al. | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Vollpe et al. | |
| 2009/0005827 A1 | 1/2009 | Weintraub et al. | |
| 2010/0007413 A1 | 1/2010 | Herleikson et al. | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0043149 A1 | 2/2014 | Cowan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0135706 A1 | 5/2016 | Sullivan et al. | |
| 2016/0256104 A1 | 9/2016 | Romem et al. | |

(56) References Cited

U.S. PATENT DOCUMENTS

| | | |
|---|---|---|
| 2016/0283900 A1 | 9/2016 | Johnson et al. |
| 2016/0303371 A1 | 10/2016 | Whiting et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0056682 A1 | 3/2017 | Kumar et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0348759 A1 | 12/2018 | Freeman et al. |
| 2018/0361165 A1 | 12/2018 | Jaax et al. |
| 2019/0030351 A1 | 1/2019 | Sullivan et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |
| 2020/0398065 A1 | 12/2020 | Engman et al. |

FOREIGN PATENT DOCUMENTS

| | | |
|---|---|---|
| JP | 4320257 A | 3/2005 |
| JP | 5963767 A | 1/2014 |
| JP | 2014526282 A | 10/2014 |
| WO | 9839061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

<u>*SAMPLE COMPONENTS OF WEARABLE CARDIOVERTER DEFIBRILLATOR (WCD) SYSTEM*</u>

*SAMPLE COMPONENTS OF EXTERNAL DEFIBRILLATOR*

COMPONENTS OF
SAMPLE WCD SYSTEM

MULTIPLE ELECTRODES FOR
SENSING ECG SIGNALS ALONG
DIFFERENT VECTORS

WEARABLE CARDIOVERTER DEFIBRILLATOR WITH AI-BASED FEATURES

CROSS-REFERENCE(S) TO RELATED APPLICATION(S)

This application is a continuation of U.S. application Ser. No. 16/946,512, filed Jun. 24, 2020, entitled WEARABLE CARDIOVERTER DEFIBRILLATOR WITH AI-BASED FEATURES, which claims the benefit of U.S. Provisional Application No. 62/865,693 filed Jun. 24, 2019, entitled WCD WITH AI-BASED FEATURES, which are expressly incorporated herein by reference in their entirety for all purposes.

SUMMARY OF THE DISCLOSURE

According to embodiments of the present disclosure, "Artificial Intelligence" or "AI" technology can be applied to Wearable Cardioverter Defibrillators ("WCDs") and other wearable medical equipment in various ways, including:

garment fitting and adjustment;

analyzing electrocardiogram ("ECG"), other sensor data and/or other patient data (e.g., age, gender, previous medical conditions, etc.) in real time to detect/assess the patient's present condition and/or need for treatment for cardiac and other conditions (e.g., stroke, coughing, apnea, etc.);

detect imminent failure of the wearable medical device components capturing and reporting data collected from the patient for presenting to clinicians adjusting thresholds for alarms and notifications based on patient's responses;

improving patient compliance based on the patient's past non-compliant behavior and actions that resulted in the patient becoming compliant;

providing tests to the patient (e.g., grip test, dexterity tests, balance tests, etc.) and learning the patient's responses to detect/assess the patient's present condition and/or need for treatment;

learning the patient's voice, activity, posture, time of day, etc. for implementing intelligent voice recognition/activation of the medical device.

DETAILED DESCRIPTION

General Background on WCDs

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
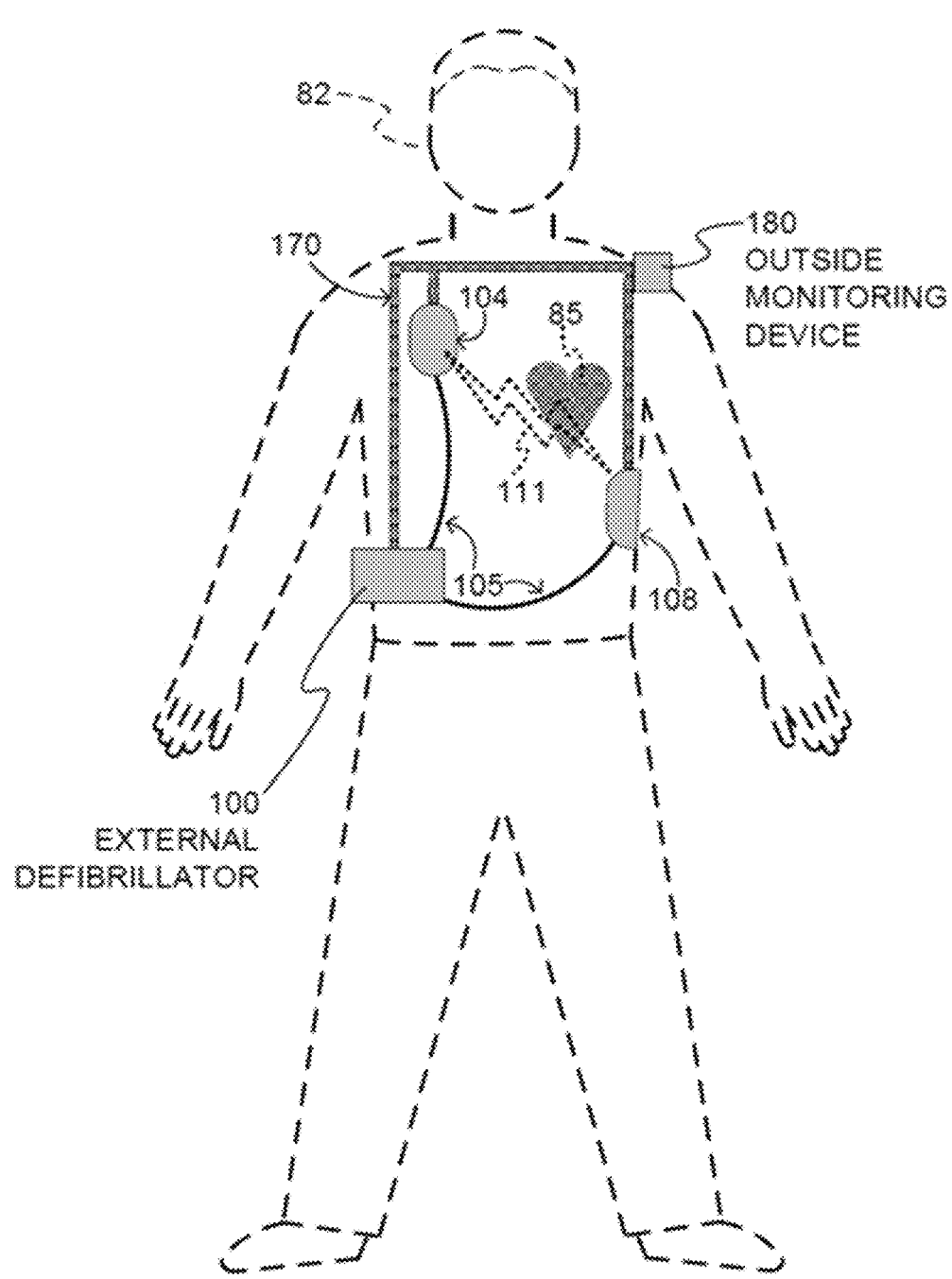
FIG. 1 is a conceptual diagram of a patient wearing a WCD, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bedridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
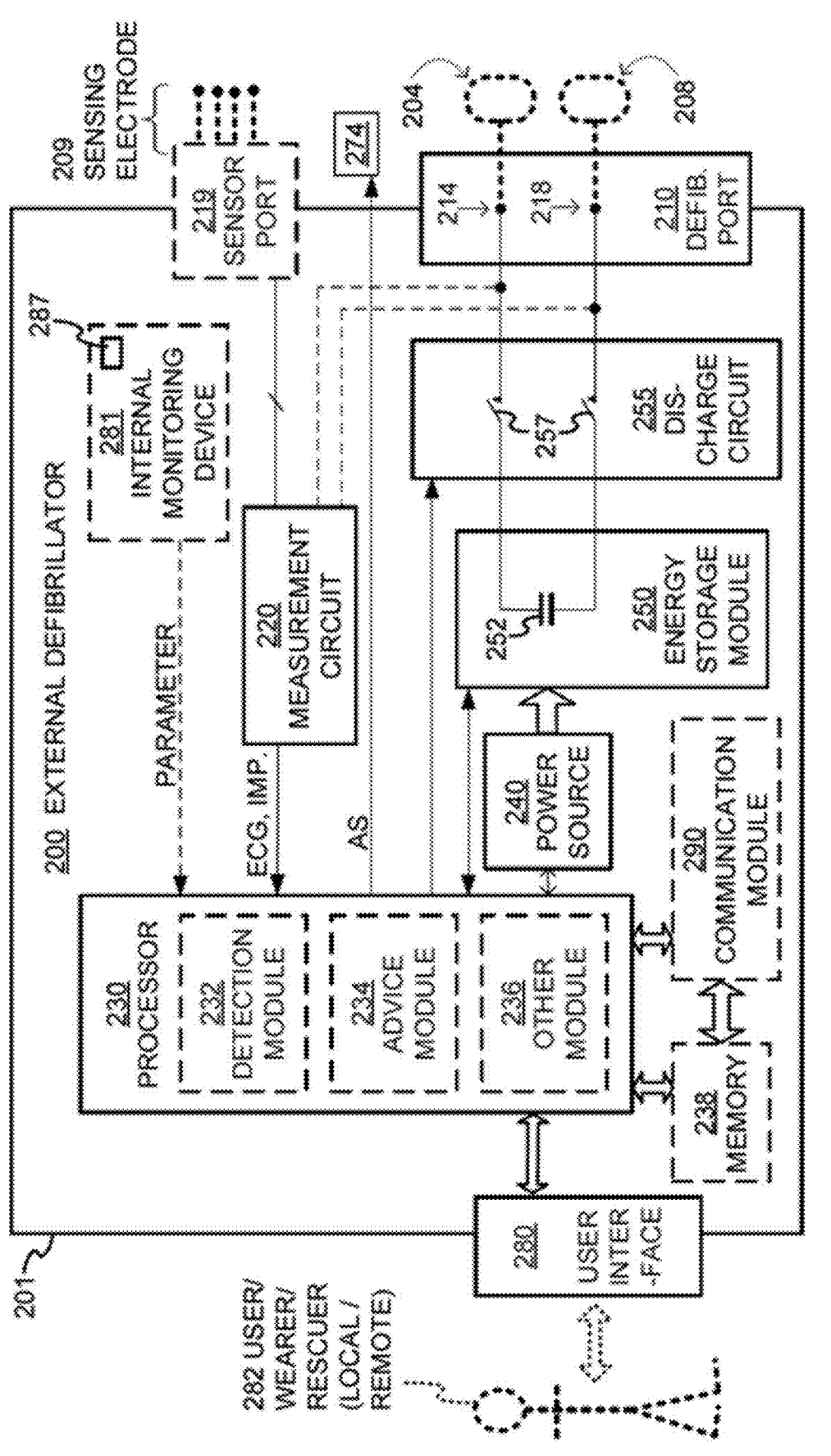
FIG. 2 is a diagram showing components of an external defibrillator, made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended to be worn by a patient, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document. If internal monitoring device 281 is indeed provided, processor 230 may receive its inputs, etc.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a nontransitory storage medium, such as memory 238 that is described more fully later in this document. Such a memory can have a nonvolatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of executable instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference for all purposes.

Processor 230 can include additional modules, such as other module 236, for other functions. In various embodiments, other module 236 may include functional instructions for performing machine learning or artificial intelligence functions. Examples of such functional instructions may be implemented as a neural network, random forest, a support vector machine, recursive partitioning, Bayesian methods, fuzzy rule-based systems, or the like. One or more of such other modules 236 may be configured to implement various embodiments of artificial intelligence functions described below.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in U.S. 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through the body of patient 82 while the support structure is being worn by patient 82, so as to deliver a therapy shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

Figure 3:
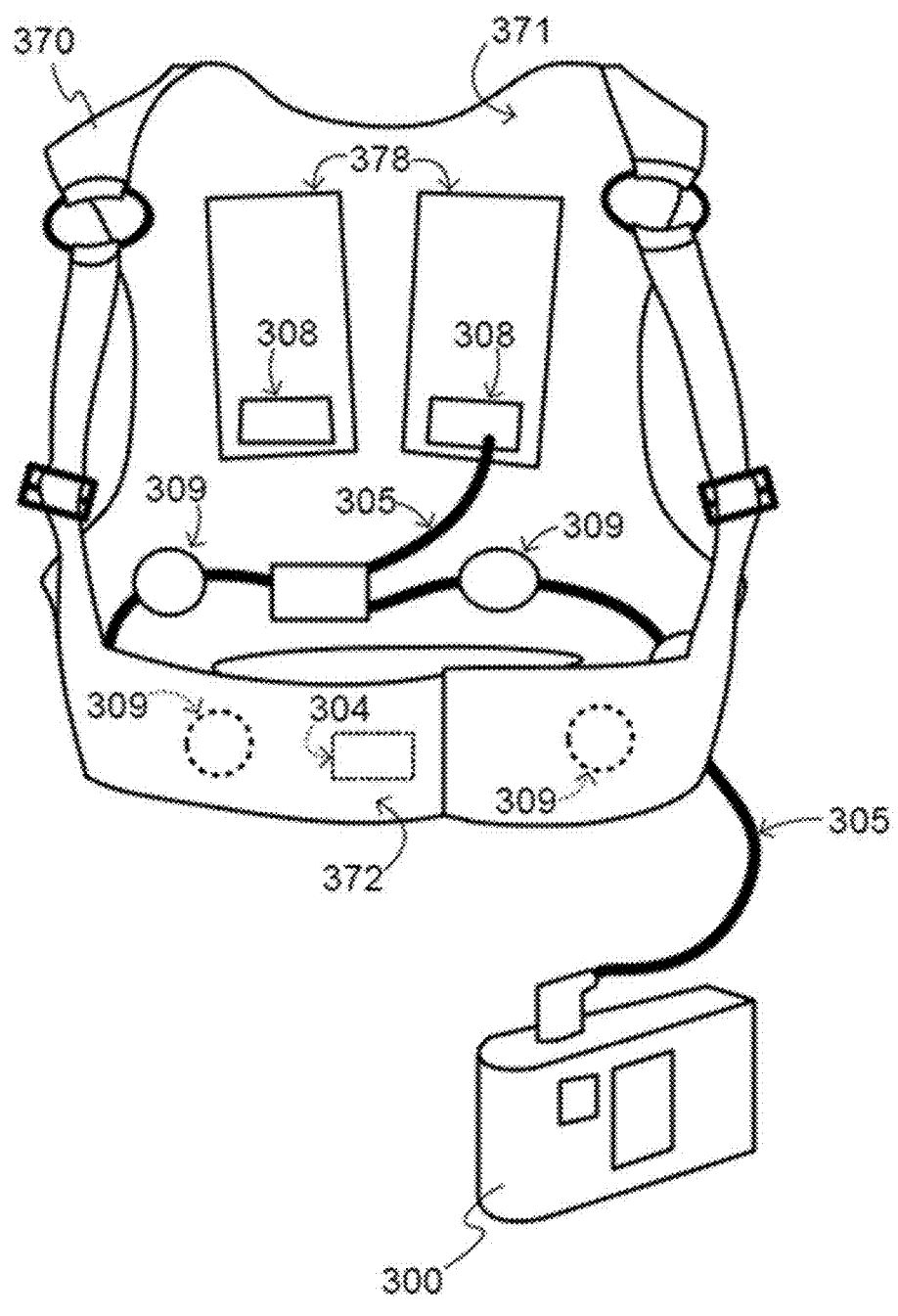
FIG. 3 is a diagram of sample embodiments of components of an WCD system.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
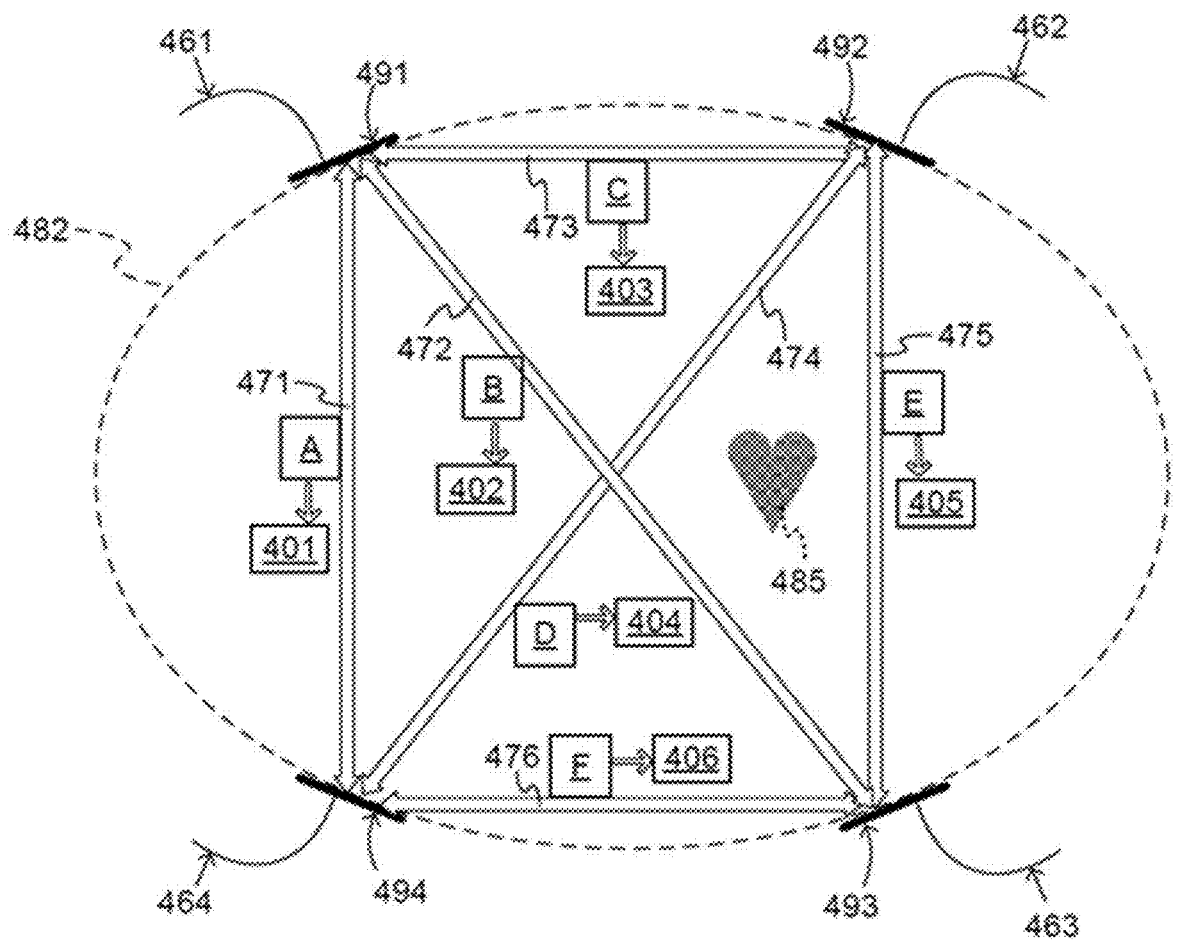
FIG. 4 is a conceptual diagram for illustrating how multiple electrodes of a WCD system may be used for sensing ECG signals along different vectors according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment. These vectors 471, 472, 473, 474, 475, 476 define channels A, B, C, D, E, F respectively.

ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either.

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLA-TOR COMPONENTS MAKING AGGREGATE SHOCK/ NO SHOCK DETERMINATION FROM TWO OR MORE ECG SIGNALS", which is incorporated herein by reference.

Figure 5:
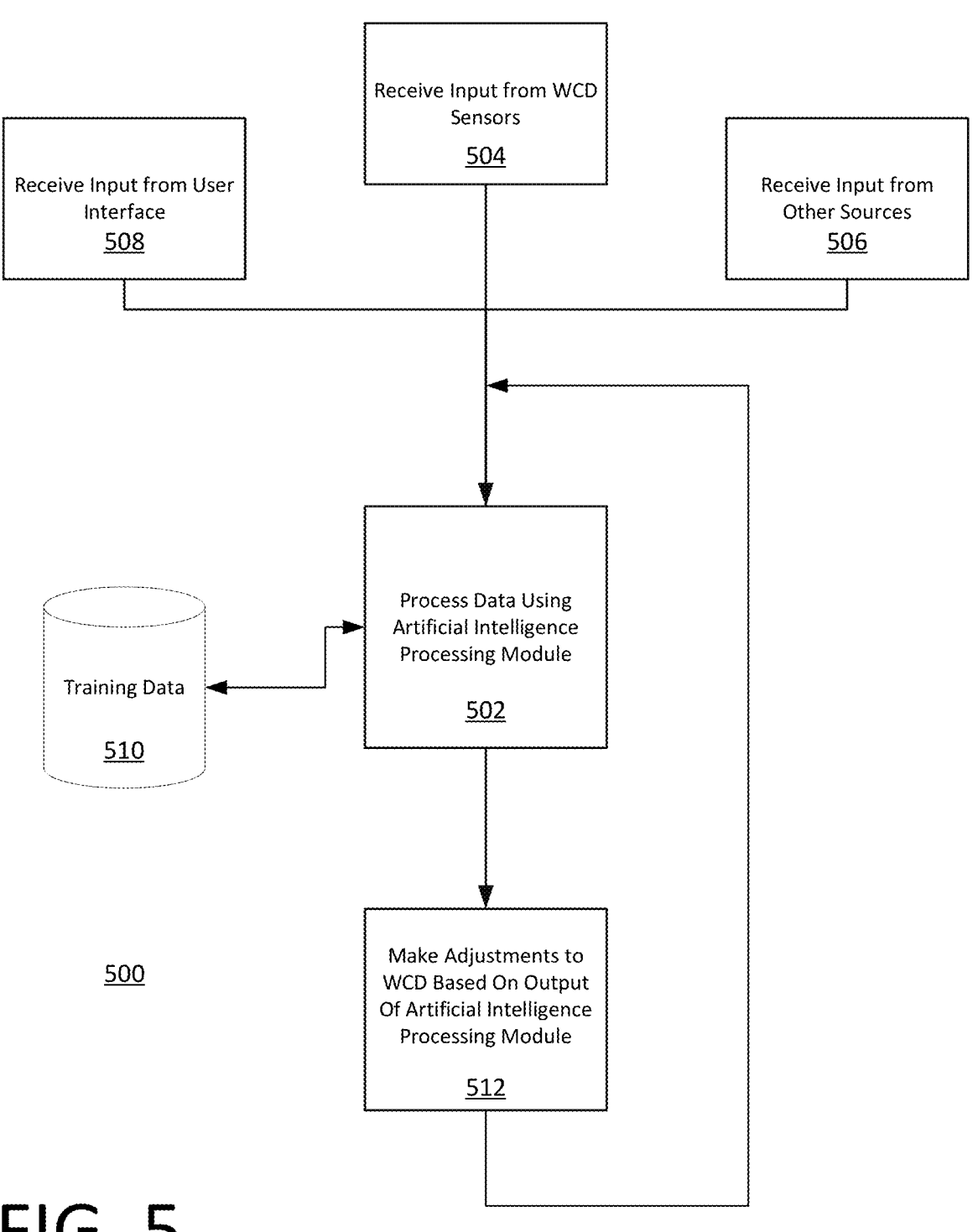
FIG. 5 is a conceptual flow diagram generally illustrating an AI process that may be implemented by various embodiments of the present disclosure.

FIG. 5 is a conceptual flow diagram generally illustrating an AI process 500 that may be implemented by various embodiments of the present disclosure. Generally stated, various embodiments may implement artificial intelligence and/or machine learning to automate and accomplish various functions of a WCD which have been heretofore impractical. Specific, non-exhaustive examples of such embodiments are provided below for completeness. These and other embodiments will be apparent to those skilled in the art upon a detailed review of this discussion.

To begin, an AI processing module 502 receives input from various sources, such as data from various WCD sensors 504 described above, and/or other sources 506. The information received from the WCD sensors 504 may take the form of environmental information (e.g., motion, temperature, humidity, or any of the other non-patient information described above) as well as patient information (e.g., heart rate, ECG, blood pressure, pulse oximetry, or any of the other patient-related information described above).

Still further, the AI processing module 502 may receive additional information from, for example, a user interface 508 or other input mechanism (e.g., communication link to a remote data source). Examples of such additional information may take the form of instructions or data provided by a user, either a local user or a remote user, that the AI processing module 502 may use for artificial processing and machine learning.

Once input data is received, the AI processing module 502 performs artificial intelligence and machine learning operations to improve, predict, and/or control operations to be performed by or on the WCD. Various specific examples of such operations will become apparent to those skilled in the art from the present disclosure. For the purpose of this general discussion, the operations performed by the AI processing module 502 may take any form, such as making determinations regarding whether to deliver therapy to a patient, improve characteristics about the WCD (e.g., for comfort or operation), better detect the operating and maintenance state of the WCD, implement instructions provided by remote users, collect and learn data about the use of the WCD or the patient, and many more.

Once the AI processing module 502 has completed its processing, generally stated, adjustments 512 may be made to the WCD to improve the operation of the WCD, the patient's wellbeing, or to other functionality provided by the WCD. Again, as described in greater detail below, many various features and functions of the WCD may benefit from the processing by the AI processing module 502. As those adjustments are made, the process 500 may return to the data input portion of the process 500. In this manner, the AI processing module 502 is constantly receiving input data, making adjustments to the WCD or the WCD system, and further refining additional adjustments. Still further, training data 510 may be used by the AI processing module 502 either to initially train the AI processing module 502 prior to use, or to improve the efficiency, accuracy, and operation of the AI processing module 502.

Specific implementations of various embodiments employing AI processing module 502 will now be described in greater detail. Each of the following illustrative embodiments may be implemented individually or in various combinations. Still further, other embodiments will become apparent to those skilled in the art from the following illustrative embodiments.

Garment Fitting Embodiments

In some embodiments of the present disclosure, artificial intelligence (AI) technology is used to improve the fit of a WCD or other patient worn medical device (collectively referred to herein as the Garment). For example, the data from patients wearing the Garment can be collected and processed using AI technology (e.g., machine learning algorithms) to improve the fit of the garment to reduce noise in sensor output signals, loss of sensor contact with the patient, comfort (as indicated by patient feedback), compliance, etc. The data includes sensor data from the sensors coupled to or integrated with the Garment, as well as other data from other sources. In some embodiments, the sensor data comprises one or more of the following: ECG, heart rate, blood pressure, patient movement, patient posture, patient's body temperature, oximetry, capnography, ambient temperature, ambient humidity, perspiration (e.g., moisture, pH, particular chemicals), atmospheric pressure, patient's vocalizations/breathing sounds (e.g., the properties of the patient's voice, snoring, breathing, sighing, coughing, etc.), or other sensor data. In embodiments, the data also comprises one or more of the patients' size, shape (e.g., by optically scanning the patient's body using a 3D body scanner such as described at https://www.aniwaa.com/best-3d-body-scanners; or an app similar to the MTailer app that uses a smartphone camera), weight, BMI, muscle mass, body fat percentage, average water weight, age, gender, fitness level, average activity level, patient's usual activities, the time of day, etc. that are not necessarily collected by garment sensors. In some embodiments, at least some of this other data is received by the Garment via a user entering the data via a user interface. In embodiments, the AI technology comprises a multi-layer neural network (example, a convolutional neural network) configured with one or more machine learning algorithms to correlate the patient data to garment parameters that best fit a particular patient. In other embodiments, AdaBoost or a support vector machine (SVM) are used. In some embodiments, the AI technology is implemented using one or more processors of the Garment, while in other embodiments, the AI technology is implemented at least in part using a cloud-based system accessible (e.g., wirelessly) by the Garment. These embodiments of the AI technology can also be used in the other embodiments described herein.

In an initial fitting process, one or more of this "non-garment" data is collected and processed by the AI technology to determine the style/dimensions/materials/features/components of a Garment that best fits the patient, and the best locations for the sensors and other components of the medical device. In some embodiments, the Garment can be custom fabricated to these dimension and sensor locations, or selected from a group of different standard sizes/configurations, or the Garment may be made with adjustable dimensions and sensor/component locations via straps, belts, laces, zippers, Velcro, removable/replaceable panels/sections/components, or a combination of standard sizes with adjustable components, etc. Afterwards, while the patient is wearing the garment, the sensor data and patient feedback is collected and processed using the AI technology to determine if the Garment dimensions and/or sensor/component placement should be adjusted. For example, if the data such as activity level, breathing sounds, snoring sounds, etc. indicate that the Garment dimensions are too tight and are restricting the patient's ability to take breath during certain activities and/or postures (e.g., walking, sleeping, sitting), the AI technology can detect these conditions and provide notifications or prompts with instructions or suggestions for adjusting the fit of the garment.

Present Condition/Treatment Embodiments

In some embodiments of the present disclosure, artificial intelligence (AI) technology is used to detect the patient's present condition and/or need for treatment for cardiac and other conditions. For example, the data from patients wearing the Garment can be collected and processed using AI technology (e.g., machine learning algorithms), along with the diagnosis and treatment data corresponding to the patient data to determine whether the patient is experiencing a condition that needs a treatment. These conditions/treatments include cardiac conditions that can be treated by a WCD, as well as other non-cardiac conditions/treatments, such as stroke, apnea, dizziness, coughing, seizures, etc. The data includes sensor data from the sensors coupled to the garment, as well as other data as described above for the Garment Fitting Embodiments. Embodiments of the AI technology are also described above in conjunction with the Garment Fitting Embodiments. Other embodiments of the AI technology can include using stochastic computing circuits (e.g., as disclosed in https://techxplore.com/news/2018-10-method-automate-synthesis-stochastic-circuits.html) to implement neural networks (e.g., as disclosed in https://ieeexplore.ieee.org/document/8119196). Some embodiments of these stochastic computing circuit-based machine learning implementations have reduced size and power requirements compared to "binary" neural networks while still having similar performance, which can be advantageous in battery powered wearable medical devices such as WCDs and particularly in adhesive systems such as being developed by Element Science. These embodiments of the AI technology can also be used in the other embodiments described herein.

The data from sensor(s) of the garment (and other sensors in some embodiments) is received and processed by the AI technology to identify a condition. In embodiments, the Garment can automatically provide a treatment for the condition, or a notification or prompt to the user or bystanders (e.g., visual via a display, or an audible message via a speaker) or remote recipients (e.g., via a communication channel such as cellular, Wi-Fi, Bluetooth, etc.). For example, some embodiments are configured to detect whether a patient is unsteady or dizzy and likely to fall and provide a notification to the user to take appropriate safety action (e.g., to sit down or find a support). Another example is an embodiment that is configured to detect if a patient is experiencing apnea and provide a notification to the user or remote clinician so that the user can be prescribed a CPAP machine or other treatment. In other embodiments the AI technology is configured to process data such as posture, heart rate, patient's voice properties (e.g., pitch, tone, rate, slurring), etc. to detect if the patient is experiencing a stroke.

Predictive Maintenance Embodiments

In some embodiments of the present disclosure, artificial intelligence (AI) technology is used to detect whether a component of the Garment is in imminent need of maintenance and if so prompt the user and/or remote entity to take a maintenance action before the component actually fails. For example, the data from sensors of the Garment generated by previous deployments of the Garments along with corresponding error/failure/maintenance data can be processed using AI technology to develop an AI algorithm that can predict an imminent failure of the Garment (or a component thereof). For example, imminent failure of an electrode connector may be associated with certain patterns of ECG noise, patient movement, cumulative wear-time, cumulative connect/disconnect cycles, ambient temperature, ambient humidity, drop detection, impedance changes, etc. that the AI technology can determine, and then use to issue prompts for connector inspection/maintenance. Other examples of "failures" that are detectable by embodiments of the present disclosure include failure of wiring/cabling between sensors and other electronics of the medical device, the battery, displays (e.g., LCD displays), touchscreens, buttons/switches, etc. In devices with moving or rotating components (e.g., fans, pumps), the data can include vibration sensor data, rotational speed data, temperature data, etc. sensed at the component that can be processed using the AI technology to predict failures and provide prompts to take appropriate maintenance action. In some embodiments in which the AI technology is local to the device (as opposed to cloud-based approaches), the AI technology is implemented using the previously described stochastic computing circuits to reduce the size and power requirements of the wearable medical device.

Data Collection Embodiments

In some embodiments of the present disclosure, artificial intelligence (AI) technology is used to capture and store data from the patient and wearable medical device, present it to the patient's doctor/clinician, and use AI technology to monitor the actions taken by the doctor/clinician in response to the data to customize the presentation of future data to that doctor/clinician. For example, in some WCD embodiments, a large amount of data from various patient physiological parameter sensors (e.g., one or more of heart rate, ECG, impedance, accelerometer, body temperature, blood pressure, oximetry, etc.) and other parameters (e.g., ambient temperature, time of day, wear-time, activity level, etc.) is available to the doctor/clinician.

The AI technology is configured to monitor the doctor/clinician's actions/responses in accessing this data and based on these actions, generate a "default" presentation of the data for this particular doctor/clinician. For example, if a doctor consistently views the patient's activity level, wear-time, heart rate and ECG data while ignoring the other data, the AI technology learns to present only the wear-time, heart rate and ECG data in a "home page" whenever the doctor/clinician accesses the patient's data.

Further, the AI technology can also be configured to learn the doctor's response to certain conditions in the "home page" data and automatically provide appropriate additional data. For example, the "home page" may include the patient's heart rate data but not activity level and QRS width data. However, when the heart rate is higher than a certain threshold, this example doctor/clinician tends to access the data for activity level and QRS width). In embodiments, the AI technology analyzes the data, learns the "conditions" for which the doctor/clinicians accesses additional data, and then automatically presents the additional data when the conditions are detected. In the above heart rate example, the AI technology learns the heart rate threshold that causes the doctor/clinician to access the activity level and QRS width data, and when the heart rate is above this threshold when the doctor/clinician accesses the "home page", the AI technology also presents the activity level and QRS width data. These embodiments can improve the efficiency of the doctor/clinician in monitoring and diagnosing the patient's condition.

Notification Adjustment Embodiments

In some embodiments of the present disclosure, AI technology is used to capture and store data related to responses of users (e.g., the patient and/or a remote person such as a family member or doctor/clinician monitoring the patient via a communication network) to notifications, alerts, alarms, prompts, etc. (also referred to as User Notifications) and based on these responses use the AI technology to customize the presentation of future User Notifications presented to each user. For example, in some embodiments, the input data for the AI technology includes:

1. the event or patient condition for which the User Notification is issued (e.g., sensor detachment, battery low, imminent therapy delivery, not wearing Garment, stop moving to reduce sensor noise, prompt to take medication, prompt to exercise, prompt to rest, prompt to contact doctor/clinician, etc.)

2. the user's action (or inaction) taken in response to the User Notification (e.g., ignoring the User Notification, disabling the User Notification without taking the appropriate responsive action, performing the appropriate responsive action after disabling the User Notification, performing the appropriate responsive action before disabling the User Notification, contacting a doctor or a family member after a User Notification, user feedback such as, for example via a "like" or "dislike" button on the UI.)

3. the user's response time to the User Notification, 4. the time of day the User Notification was provided, 5. the patient's activity and/or posture when the User Notification was provided (e.g., exercising, sleeping, laying down, sitting, traveling in a vehicle, etc.)

6. the type of User Notification, which can include one or more of:

a. audio (such as voice prompt, tones, beeps, combinations thereof, etc.)

b. visual (such as flashing or continuous lights, textual, graphical, combinations thereof), c. physical (such as intermittent or continuous vibration, haptic, gyroscopic, small electric shocks, etc.).

The AI technology is configured to monitor this data and based on these actions, learn the Users' responses to the various User Notifications and customize the User Notifications for each user to achieve the best user response under the current conditions. For example, the AI technology can learn that at night while sleeping, a particular patient does not respond quickly to audio User Notifications but will respond quickly to flashing light User Notifications and configure the medical device to issue flashing light User Notifications when needed while the patient is sleeping at night. In another example, the AI technology can learn that while exercising a particular patient does not detect or responds slowly to audio and visual User Notifications but does respond quickly to both low power and high power intermittent vibration User Notifications. The AI technology can configure the medical device to issue low power level vibrations when needed while the patient is exercising, which can also advantageously save power while still achieving a fast response time from the patient.

In some embodiments, the above data from previous patients is processed using AI technology to determine default sets of User Notifications for categories of patients and users. At an initial fitting of the Garment to a patient, the category that the patient most closely matches is determined and the Garment is initially configured with the User Notifications for that category. In embodiments, the AI technology for that Garment then operates as described above to customize the User Notifications for that patient and other users associated with that Garment. For example, in some embodiments the AI technology is used to identify User Notifications that work best for improving patient compliance. The patient compliance User Notifications (e.g., periodic reminders, prompts when non-compliance is detected, substantially simultaneous or concurrent notifications to family members and/or the patient's doctor) issued to previous patients and how quickly and well the patient responded to these compliance User Notifications is collected and processed by AI technology to determine default sets of patient compliance User Notifications for categories of patients and associated users.

Patient Testing Embodiments

In some embodiments of the present disclosure, AI technology is used in conjunction with one or more tests provided to the patient. The patient's responses to the test(s) along with other data are processed using AI technology to detect or assess the patient's present condition and/or need for treatment. In embodiments, the tests include one or more of: a grip test; a manual dexterity test; a balance test; a following instructions test; tests to determine whether the patient can perceive the various types of User Notifications that the Garment can provide to the patient, etc. The AI technology processes data associated with these tests from previous patients that used the Garment (and the current patients' previous test responses in some embodiments) to identify the patient's current condition and whether a treatment, notification or further testing is appropriate for the patient. For example, some studies (e.g., https://www.health.harvard.edu/blog/grip-strength-may-provide-clues-to-heart-health-201505198022) have shown that grip strength is a good indicator of cardiovascular disease. The Garment's AI technology can be configured to receive and process the test results and other data (e.g., the patient gender, age, weight, health history, time of day, ambient temperature, etc.) to assess the patient's cardiac condition. The Garment can use the assessment to take appropriate actions such as providing notifications to the patient or a remote user (e.g., the patient's doctor). Balance and mobility tests can be used to assess the patients risk of falling and provide appropriate action and to assess whether a patient's fall is due to the patient becoming unconscious vs be conscious and falling due to being unbalanced. In some embodiments, the AI technology can use the testing data and other patient data as part of a patient recovery or rehabilitation program, to prompt, encourage and/or instruct the patient on the appropriate exercises/activities and the amount of exertion or energy the patient should use in these exercises/activities that aid the patient's progress in the recovery/rehabilitation program.

Voice Recognition Embodiments

In some embodiments of the present disclosure, AI technology is used to recognize the patient's voice for implementing voice recognition, activation and control of the Garment. In some embodiments, the Garment's AI technology is configured to enable the Garment to listen via a microphone for voice commands to appropriately respond to questions from patients and their medical advisors (vs questions from bystanders) to assist the patient while protecting the patients' privacy. In some embodiments, the Garment's AI technology is configured to also "listen" to other audio data to provide context for the voice commands to provide more accurate/appropriate responses to the voice commands. For example, the patient may use a voice command to ask for assistance because the patient is not feeling well. When the audio data indicates that the patient is in a public area, the Garment can be configured to emit requests to bystanders to call 911. But if the audio data indicates the patient is at home alone, the Garment can be configured to transmit the request to family members via a wireless communication link.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A Wearable Cardioverter Defibrillator (WCD) system, comprising:

a support structure configured to be worn by a patient;

an energy storage module;

a discharge circuit coupled to the energy storage module;

a plurality of sensors configured to render a first input regarding a parameter of the patient associated with patient health, a first sensor in the plurality of sensors being operative to detect one or more physiological conditions of the patient, a second sensor in the plurality of sensors being operative to detect one or more environmental conditions, the one or more physiological conditions including at least a heart rhythm of the patient, the one or more environmental conditions including at least one of motion or location of the patient;

a data input source, in communication with a remote data provision service, configured to render a second input regarding the parameter of the patient associated with the patient health; and one or more processors configured to:

receive the first input from the plurality of sensors and the second input from the data input source;

determine that the patient is experiencing a condition based on the received first input and the second input;

responsive to the determination that the patient is experiencing the condition, determine a baseline treatment for the condition based on the first input and the second input;

provide the first input and the second input to an Artificial Intelligence (AI) processing module, the AI processing module being configured to analyze the first input and the second input, and adjust the baseline treatment based on the analysis by the AI processing module, wherein the AI processing module is configured to adjust the baseline treatment upon determining a deterioration in the patient health; and initiate a shock therapy to the patient by causing the discharge circuit to discharge an electrical charge from the energy storage module to the patient while the support structure is being worn by the patient, in response to the adjusted baseline treatment comprising shocking the patient.

2. The WCD system of claim 1, wherein the condition is informed by the one or more physiological conditions, the one or more environmental conditions, or a combination thereof.

3. The WCD system of claim 1, wherein the one or more physiological conditions further comprise at least a posture of the patient.

4. The WCD system of claim 1, wherein the condition is apnea.

5. The WCD system of claim 1, wherein the condition is stroke.

6. The WCD system of claim 1, wherein the one or more processors are further configured to provide a treatment for the condition based on the adjusted baseline treatment.

7. The WCD system of claim 6, wherein the treatment comprises the shock therapy.

8. The WCD system of claim 1, wherein the adjusted baseline treatment comprises providing a notification.

9. The WCD system of claim 8, wherein the notification comprises instructions to the patient, a bystander, or a remote recipient to provide a treatment.

10. The WCD system of claim 8, wherein the notification comprises information to enable a remote clinician to prescribe a treatment.

11. The WCD system of claim 8, wherein the notification comprises instructions to the patient to take a safety action.

12. The WCD system of claim 1, wherein the data input source is collocated with at least one of the one or more processors.

13. The WCD system of claim 1, wherein the one or more processors are two or more processors, and wherein a first of the two or more processors is configured to implement the AI processing module and to make the adjustments to the baseline treatment.

14. The WCD system of claim 13, wherein a second of the two or more processors is configured to initiate the shock therapy.

15. The WCD system of claim 1, wherein the condition is dizziness.

16. The WCD system of claim 1, wherein the WCD system further comprises a sound sensor, wherein the sound sensor is configured to sense one or more patient voice properties, and wherein the one or more patient voice properties include pitch, tone, rate, or slurring of a patient's voice.

17. The WCD system of claim 16, wherein the condition is informed by the one or more patient voice properties.

18. The WCD system of claim 1, wherein the condition is coughing.

19. The WCD system of claim 1, wherein the condition is seizure.

20. The WCD system of claim 1, wherein the first input and the second input comprise quantitative and measurable data.

* * * * *